United States Patent
Okayasu

(10) Patent No.: US 10,936,890 B2
(45) Date of Patent: Mar. 2, 2021

(54) VEHICLE DEVICE

(71) Applicant: DENSO CORPORATION, Kariya (JP)

(72) Inventor: Takafumi Okayasu, Kariya (JP)

(73) Assignee: DENSO CORPORATION, Kariya (JP)

( * ) Notice: Subject to any disclaimer, the term of this patent is extended or adjusted under 35 U.S.C. 154(b) by 162 days.

(21) Appl. No.: 16/211,300

(22) Filed: Dec. 6, 2018

(65) Prior Publication Data

US 2019/0108407 A1    Apr. 11, 2019

Related U.S. Application Data

(63) Continuation of application No. PCT/JP2017/019016, filed on May 22, 2017.

(30) Foreign Application Priority Data

Jun. 9, 2016 (JP) .............................. JP2016-115310

(51) Int. Cl.
*G06K 9/00* (2006.01)
*A61B 5/024* (2006.01)
(Continued)

(52) U.S. Cl.
CPC ........ *G06K 9/00885* (2013.01); *A61B 5/0013* (2013.01); *A61B 5/024* (2013.01);
(Continued)

(58) Field of Classification Search
CPC ....... A61B 5/02438; A61B 5/024; A61B 5/18; A61B 5/02; A61B 5/1176; A61B 5/02416;
(Continued)

(56) References Cited

U.S. PATENT DOCUMENTS 9,037,125 B1 *    5/2015    Kadous ............. H04M 1/72577
                                                        455/418
2014/0303899 A1 *  10/2014   Fung ....................... G06F 19/36
                                                          702/19
(Continued)

FOREIGN PATENT DOCUMENTS

| JP | 2003339681 A | 12/2003 |
| JP | 2005169980 A | 6/2005 |

(Continued)

OTHER PUBLICATIONS

Chandler, Clive, and Rachel Cornes. "Biometric measurement of human emotions." International Journal of Computing Science and Communication Technologies 4.2 (2012): 5. (Year: 2012).*

(Continued)

*Primary Examiner* — Geoffrey E Summers
(74) *Attorney, Agent, or Firm* — Harness, Dickey & Pierce, P.L.C.

(57) ABSTRACT

A vehicle device receives image data transmitted from a compartment camera photographing a driver. The vehicle device analyzes the image data received from the compartment camera, and detects a heart rate of the driver. The vehicle device wirelessly communicates with one or more wearable devices possessed by one or more people who ride on a vehicle. The vehicle device identifies a wearable device possessed by the driver by comparing biometric information transmitted from the one or more wearable devices with the heart rate of the driver.

4 Claims, 7 Drawing Sheets

(51) Int. Cl.
*A61B 5/00* (2006.01)
*A61B 5/1171* (2016.01)
*A61B 5/16* (2006.01)
*A61B 5/18* (2006.01)
*H04M 11/00* (2006.01)
*G06F 3/01* (2006.01)
*H04W 4/48* (2018.01)
*G06F 16/58* (2019.01)
*B60R 16/037* (2006.01)

(52) U.S. Cl.
CPC ...... *A61B 5/02416* (2013.01); *A61B 5/02438* (2013.01); *A61B 5/1176* (2013.01); *A61B 5/165* (2013.01); *A61B 5/18* (2013.01); *A61B 5/6801* (2013.01); *A61B 5/6893* (2013.01); *G06F 3/01* (2013.01); *G06F 3/011* (2013.01); *G06F 16/5866* (2019.01); *G06K 9/00838* (2013.01); *G06K 9/00845* (2013.01); *H04M 11/00* (2013.01); *H04W 4/48* (2018.02); *B60R 16/037* (2013.01); *G06F 2203/011* (2013.01); *G06K 9/00255* (2013.01); *G06K 9/00315* (2013.01); *G06K 2009/00939* (2013.01)

(58) Field of Classification Search
CPC ..... A61B 5/6801; A61B 5/0013; A61B 5/165; A61B 5/6893; G06K 9/00838; G06K 2209/00939; G06K 9/00885; G06K 9/00845; G06K 9/00255; G06K 9/00315; G06K 9/00288; G06K 9/00832; H04M 11/00; G06F 2203/011; G06F 3/01; G06F 16/5866; G06F 3/0304; G06F 3/015; G06F 3/011; H04W 4/48; B60R 16/037
USPC .................................................. 382/115, 104
See application file for complete search history.

(56) References Cited

U.S. PATENT DOCUMENTS

2014/0310788 A1* 10/2014 Ricci ................ H04W 12/0808
  726/6
2015/0127215 A1    5/2015 Chatterjee
2018/0360387 A1* 12/2018 Bulut ...................... A61B 5/18

FOREIGN PATENT DOCUMENTS

| JP | 4235843 B2 | 3/2009 | |
| JP | 2011172195 A | 9/2011 | |
| JP | 2014004860 A | 1/2014 | |
| JP | 2014200681 A | 10/2014 | |
| JP | 2014221172 A | 11/2014 | |
| JP | 2015089808 A | 5/2015 | |
| JP | 2016018474 A | 2/2016 | |
| WO | WO-2014145204 A1 * | 9/2014 | ............. G16H 50/20 |

OTHER PUBLICATIONS

Sun, Yu, and Nitish Thakor. "Photoplethysmography revisited: from contact to noncontact, from point to imaging." IEEE Transactions on Biomedical Engineering 63.3 (2015): 463-477. (Year: 2015).*

Israel, Steven A., et al. "Fusing face and ECG for personal identification." 32nd Applied Imagery Pattern Recognition Workshop, 2003. Proceedings . . . IEEE, 2003. (Year: 2003).*

Singh, Yogendra Narain, Sanjay Kumar Singh, and Phalguni Gupta. "Fusion of electrocardiogram with unobtrusive biometrics: An efficient individual authentication system." Pattern Recognition Letters 33.14 (2012): 1932-1941. (Year: 2012).*

* cited by examiner

VEHICLE DEVICE

CROSS REFERENCE TO RELATED APPLICATIONS

The present application is a continuation application of International Patent Application No. PCT/JP2017/019016 filed on May 22, 2017, which designated the United States and claims the benefit of priority from Japanese Patent Application No. 2016-115310 filed on Jun. 9, 2016. The entire disclosures of all of the above applications are incorporated herein by reference.

TECHNICAL FIELD

The present disclosure relates to a vehicle device that communicates with wearable devices possessed by people who ride on a vehicle.

BACKGROUND ART

A vehicle device that identifies a wearable device of a driver among multiple wearable devices brought into a vehicle has been provided.

SUMMARY

In the present disclosure, a vehicle device is provided. The vehicle device identifies a wearable device possessed by a driver by comparing biometric information transmitted from one or more wearable devices brought into a vehicle with the heart rate of the driver.

BRIEF DESCRIPTION OF DRAWINGS

The above and other objects, features and advantages of the present invention will become more apparent from the following detailed description made with reference to the accompanying drawings. In the drawings.

DETAILED DESCRIPTION

A number of people can ride on the vehicle, so that there is a possibility that multiple wearable devices are brought into the vehicle. Thus, a technique that identifies a wearable device of a driver among the multiple wearable devices brought into the vehicle has been required.

For example, in a device, a face image of the driver is registered in a portable terminal (corresponding to a wearable device). The device compares a face image of the driver photographed by a vehicle camera with the face image registered in the portable terminal. When the face images match, the device determines that the portable terminal in which the matched face image is registered is possessed by the driver.

Further, in another device, multiple seating positions in a vehicle are associated with the multiple portable terminals. When the driver sits in the driver's seat, the portable terminal associated with the seat position of the driver's seat is determined as the mobile terminal of the driver.

In the former device, the face image of the driver is not registered in the normal wearable device, so that there is a difficulty in communicating with the wearable device. Further, in the latter device, when another person different from the usual driver is seated in the driver's seat, the correspondence between the seat position and the portable terminal changes. Thus, when the correspondence has not been updated, there is a possibility that the device performs erroneous determination.

The present disclosure provides a vehicle device capable of determining a wearable device possessed by a driver when multiple wearable devices are brought into the vehicle.

First Embodiment

Figure 1:
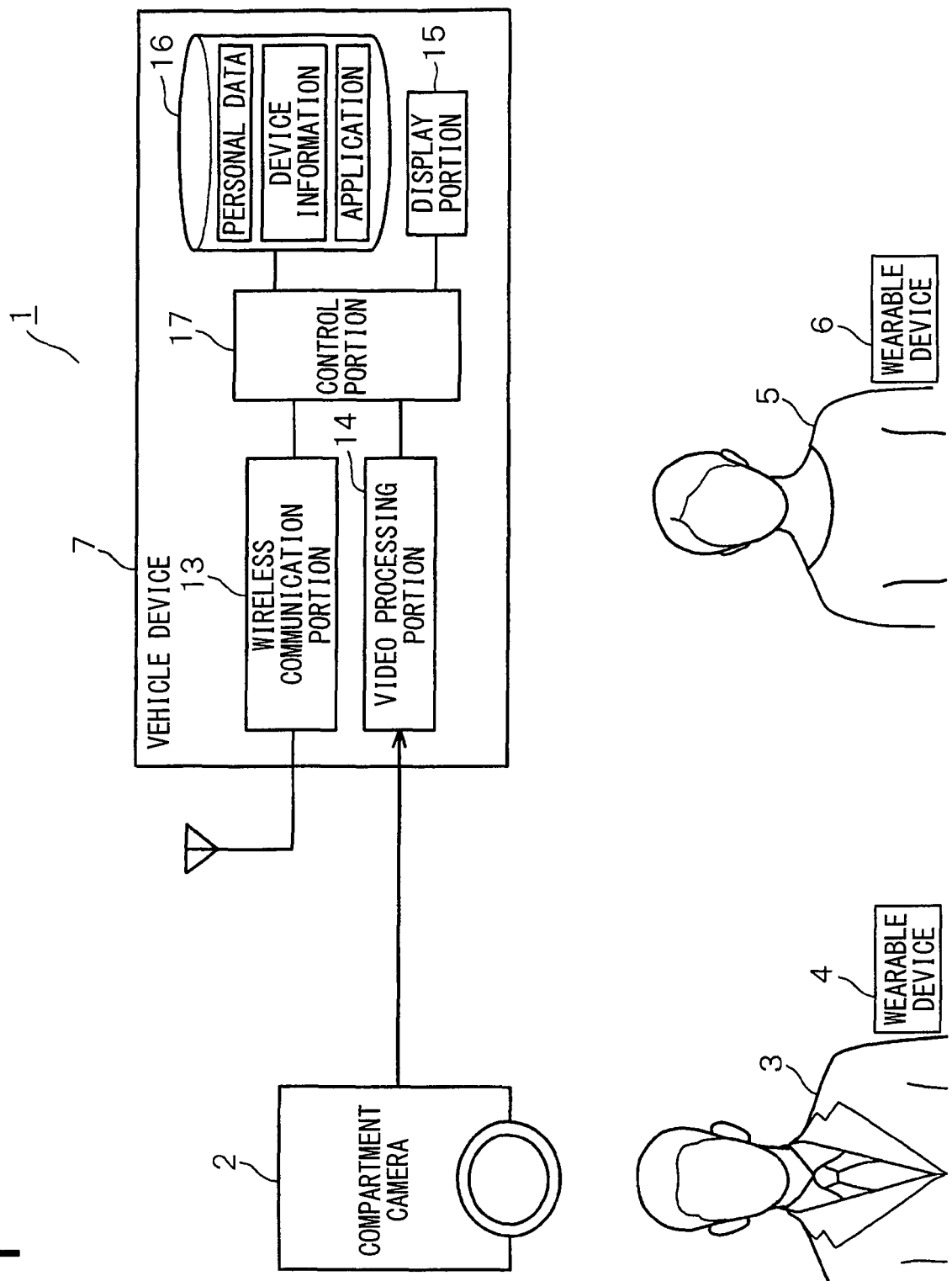
FIG. 1 is a block diagram showing a vehicle system according to a first embodiment.

The first embodiment of the present disclosure will be described with reference to FIGS. 1 to 8. As shown in FIG. 1, a vehicle system 1 of the present embodiment includes a compartment camera 2, a wearable device 4 possessed by a driver 3, a wearable device 6 possessed by a passenger 5, and a vehicle device 7.

The compartment camera 2 is provided by a camera for photographing the face of the driver 3 sitting in the driver's seat. The compartment camera 2 may be provided by a 2D camera (for example, an RGB camera), a 3D camera (for example, an infrared camera), or a camera that includes both the 2D camera and the 3D camera. The image data of the driver 3 photographed by the compartment camera 2 is transmitted to the vehicle device 7 using a video transmission technique such as LVDS (Low Voltage Differential Signaling).

The wearable device 4 of the driver 3 is provided by a wristband (including a watch), eyeglasses, clothes or the like, and is worn by the driver 3. The wearable device 4 includes a sensor that detects biometric information such as heart rate, body temperature, pulse rate, or blood pressure of the driver 3. The wearable device 4 transmits the detected biometric information data to the vehicle device 7 by wireless communication (for example, Bluetooth wireless standard). Bluetooth is a registered trademark. In the present embodiment, BLE (Bluetooth Low Energy) may be employed among Bluetooth wireless standards. Alternatively, the communication may be performed using another wireless standard such as wireless LAN.

Figure 2:
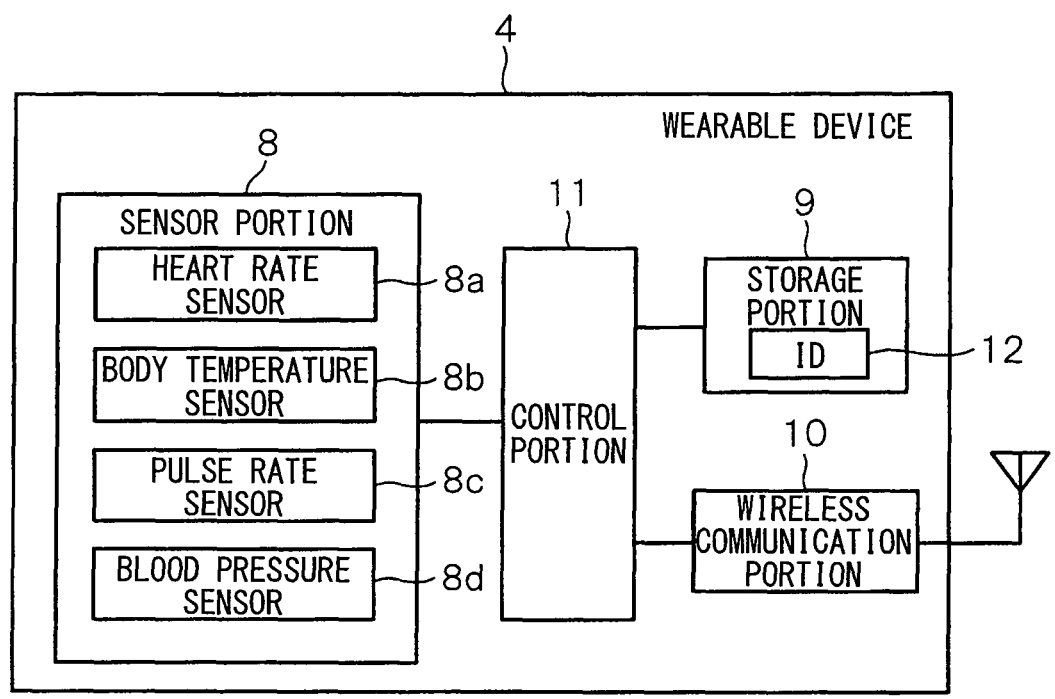
FIG. 2 is a block diagram showing a wearable device.

As shown in FIG. 2, the wearable device 4 includes a sensor portion 8, a storage portion 9, a wireless communication portion 10, and a control portion 11. The sensor portion 8 includes a heart rate sensor 8a, a body temperature sensor 8b, a pulse rate sensor 8c, and a blood pressure sensor 8d. The storage portion 9 is provided by a RAM, a ROM, a flash memory, or the like. The storage portion 9 stores an ID 12 of the wearable device 4, and temporarily stores various types of data for control and various types of biometric information data detected by sensor portion 8. The wireless communication portion 10 wirelessly communicates with the vehicle device 7 according to the wireless standard of BLE. The control portion 11 controls the entire wearable device 4.

Multiple people are capable of riding on the vehicle as the passengers 5, and each of the passengers 5 is capable of possessing the wearable device 6. Thus, multiple wearable devices 6 may be brought into the vehicle, and each of the multiple wearable devices 6 is capable of wirelessly communicating with the vehicle device 7. The configuration of the wearable device 6 is similar to the configuration of the wearable device 4 shown in FIG. 2. Each of the wearable devices 4, 6 has a unique ID 12 which is capable of being identified from one another.

The vehicle device 7 may be provided by a car navigation device. The vehicle device 7 includes a wireless communication portion 13, a video processing portion 14, a display portion 15, a memory portion 16, and a control portion 17. The vehicle device 7 further includes a position detection portion, a destination input portion, a route calculation portion, a route guide portion, and a map data input portion, each of which is included in a normal car navigation device. The position detection portion, the destination input portion, the route calculation portion, the route guide portion, and the map data input portion are not shown in FIG. 1.

The wireless communication portion 13 wirelessly communicates with each of the wearable devices 4, 6 brought into the vehicle according to the wireless standard of, for example, BLE. The wireless communication portion 13 receives various types of biometric information data and the like detected by the sensor portion 8 of each of the wearable devices 4, 6. Various types of received biometric information data and the like are stored and accumulated in the storage portion 16 by each of the wearable devices 4, 6.

The image processing portion 14 receives the face image data of the driver 3 photographed by the compartment camera 2. The video processing portion 14 analyzes the received face image data of the driver 3 so as to identify the driver 3, determine the emotion of the driver 3, detect the heart rate of the driver 3, and detect the visual line of the driver 3. The video processing portion 14 corresponds to an image processing portion.

In the configuration, the processing of identifying the driver 3 based on the face image data of the driver 3 is categorized in a biometric authentication processing. In advance, the video processing portion 14 analyzes a shape or a position of each of multiple feature points, such as an outline, an eye, a nose, or a mouth, in the photographed face image of the driver 3, and stores the analyzed data of the shape or the position of each of the multiple feature points in the storage portion 16 as personal data of the driver 3. When identifying the driver 3 based on the received face image data of the driver 3, the video processing portion 14 analyzes the received face image data of the driver 3, and compares the analyzed image data with the personal data stored in the storage portion 16 with respect to the data of the shape or the position of each of the multiple feature points. Thus, the configuration is capable of identifying the driver 3. The compartment camera 2 may be provided by the 2D camera. When the compartment camera 2 is provided by the 3D camera (that is, the infrared camera), the face stereoscopic information is capable of being analyzed and compared with the personal data. Thus, the 3D camera can improve the accuracy of individual identification.

For the processing of determining the emotion of the driver 3 based on the face image data of the driver 3, the technique described in JP 2015-169980 A may be employed. In the technique, the motion of the eyebrow, the mouth, the head, the eye or the like in the face of the driver 3 is captured. Thus, the configuration is capable of determining the emotion of the driver 3, such as "angry", "scared", "enjoying," "sad," "surprised", or "calm".

In addition, in the processing of detecting (that is, grasping) the heart rate of the driver 3 based on the face image data of the driver 3, the technique of XboxOne kinect may be employed. XboxOne kinect is a registered trademark. In this technique, the 2D camera and the 3D camera of the compartment camera 2 photographs the skin of the driver 3. With the configuration, the heart rate, the pulse rate, or the like can be measured based on subtle change of the blood flow. The technique for measuring the pulse rate in real time based on the face image, which is developed by Fujitsu Ltd., may be employed.

The display portion 15 may be provided by a liquid crystal display or the like, and displays various types of messages, images, maps, routes, and the like. The storage portion 16 is provided by a RAM, a ROM, a flash memory, or the like. The storage portion 16 stores the personal data of the driver 3, the device information of the vehicle device 7, the face image data of the driver 3, the biometric information data of the driver 3, the biometric information data of the passenger 5, various types of the application programs, various types of the control data, or the like. The control portion 17 controls the entire vehicle device 7. The control portion 17 functions as a wearable device identification portion, an activation portion, a determination portion, and a driver seat determination portion.

Figure 3:
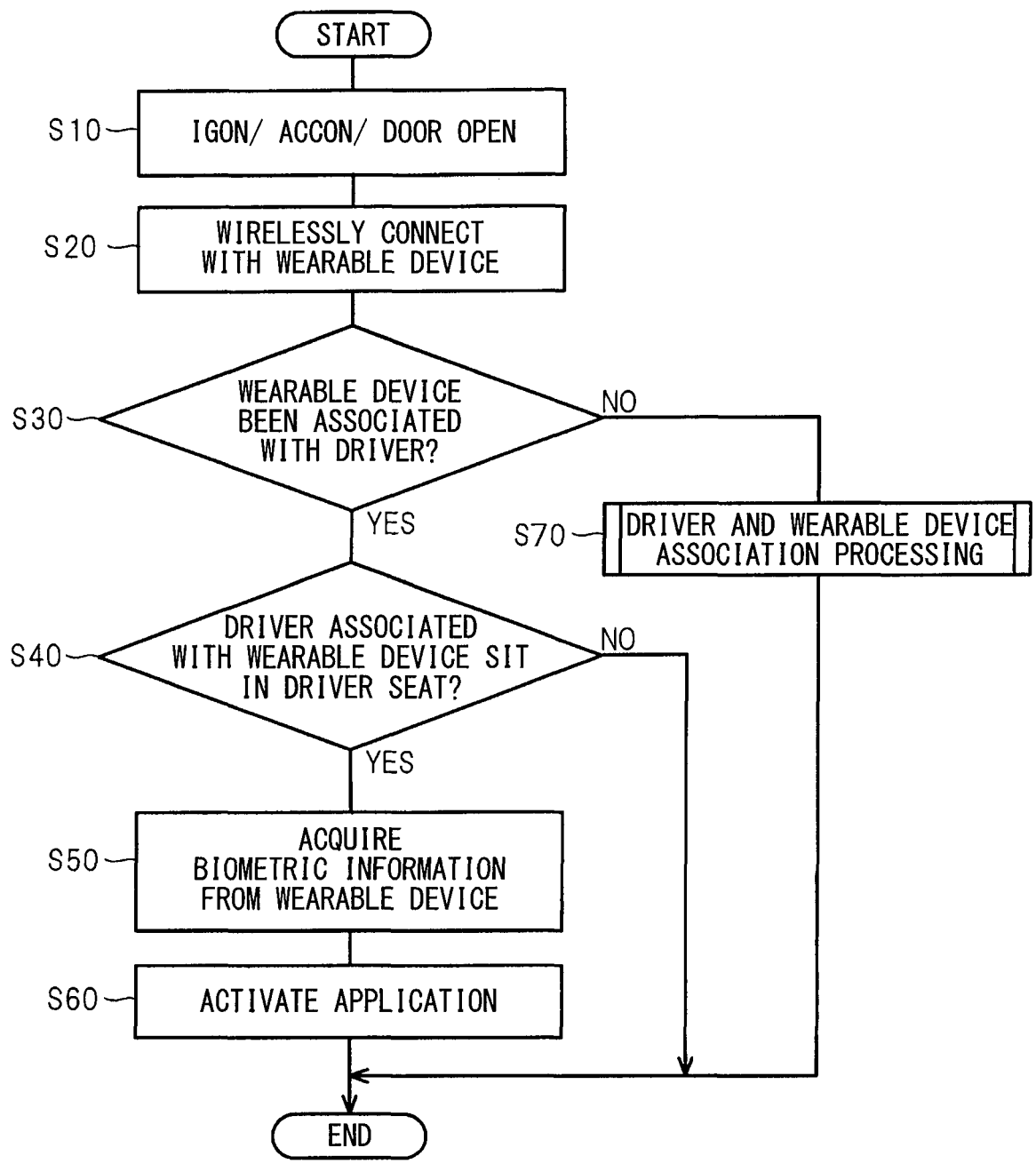
FIG. 3 is a flowchart showing a wearable device connection control.
Figure 4:
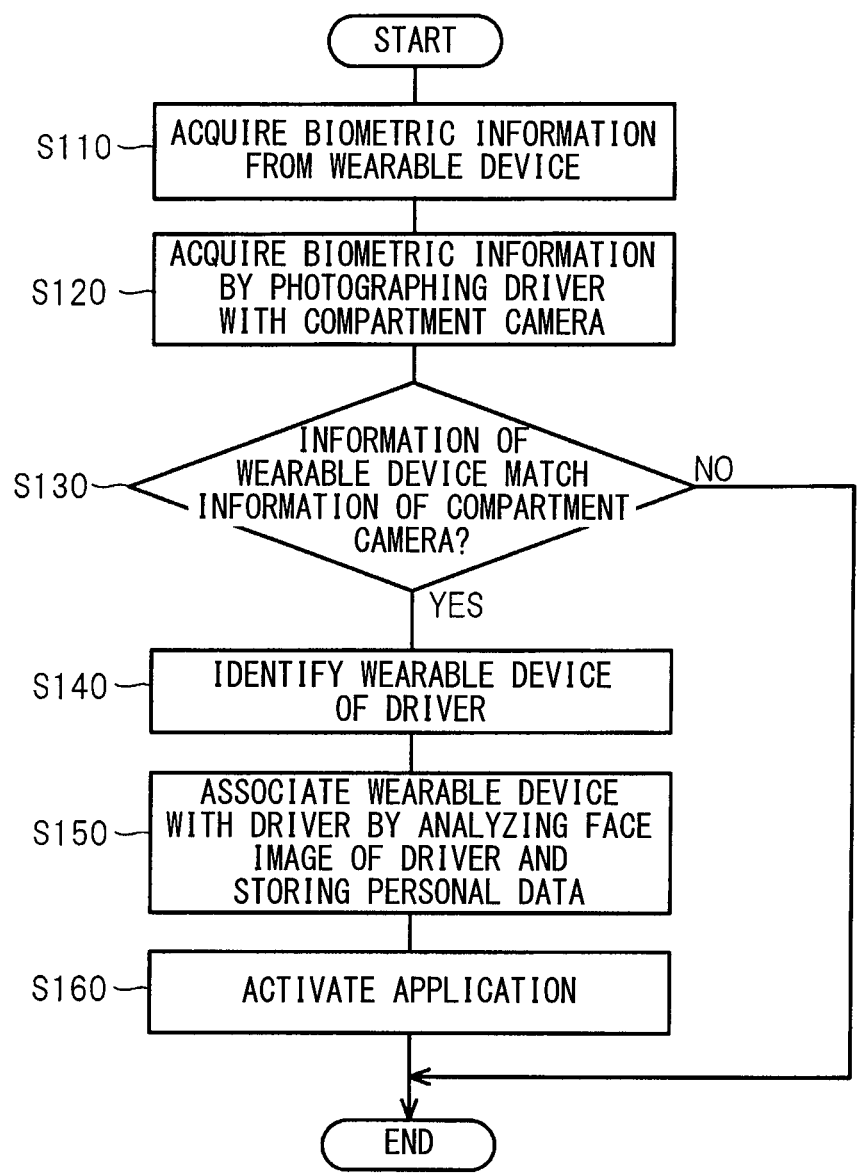
FIG. 4 is a flowchart showing an association control.

Next, the operation of the above configuration will be described with reference to FIG. 3 to FIG. 8C. The flowcharts of FIG. 3 and FIG. 4 show the control of the vehicle device 7. In S10 of FIG. 3, the user may turn on an ignition switch (that is, IGON), turn on an accessory switch (that is, ACCON), or open the door (that is, door open), and the vehicle device 7 receives a wakeup signal by CAN (Controller Area Network) communication. With this configuration, the vehicle device 7 is turned on and the vehicle device 7 is activated.

In S20, the vehicle device 7 is wirelessly connected with the wearable devices 4, 6 brought into the vehicle. In S30, the control portion 17 of the vehicle device 7 determines whether there is the wearable device 4 that has been associated with the driver 3 among the wirelessly connected wearable devices 4, 6. The association processing between the driver 3 and the wearable device 4 will be described later.

When the control portion 17 of the vehicle device 7 determines that there is the wearable device 4 that has been associated with the driver 3 (S30:YES), the procedure proceeds to S40. In S40, the control portion 17 of the vehicle device 7 determines that the person (that is, the driver 3) associated with the wearable device 4 is sitting in the driver's seat based on the face image of the driver photographed by the compartment camera 2. When the control portion 17 of the vehicle device 7 determines that the associated driver 3 is sitting in the driver's seat (S40:YES), the procedure proceeds to S50. In S50, the vehicle device 7 acquires the biometric information, such as the heart rate, the body temperature, the pulse rate, or the blood pressure of the driver 3 from the wearable device 4 of the driver 3, and stores the biometric information in the storage portion 16.

In S60, the control portion 17 of the vehicle device 7 activates an application program that executes a predetermined processing using the biometric information of the driver 3. In this case, an application program that urges the driver to pay attention to the safe driving using the heart rate or the like of the driver 3 may be executed. Then, the control ends. In S40, when the control portion 17 of the vehicle device 7 determines that the driver 3 associated with the wearable device 4 is not sitting in the driver's seat, the control portion 17 of the vehicle device 7 does not activate the application program and the control ends.

In S30, the control portion 17 of the vehicle device 7 determines that there is no wearable device 4 that has been associated with the driver 3, the procedure proceeds to S70. In S70, the vehicle device 7 executes the processing (that is, control) which associates the driver 3 with the wearable device 4.

The association processing between the driver 3 and the wearable device 4 will be described with reference to the flowchart of FIG. 4. In S110 of FIG. 4, the wireless communication portion 13 of the vehicle device 7 acquires the biometric information, such as the heart rate, the body temperature, the pulse rate, the blood pressure from all the wearable devices 4, 6 in the vehicle, and stores the biometric information in the storage portion 16.

In S120, the compartment camera 2 photographs the face of the driver 3, the video processing portion 14 of the vehicle device 7 receives the photographed face image of the driver 3, and analyzes the received face image of the driver 3. With this configuration, the video processing portion 14 of the vehicle device 7 acquires the information of the heart rate of the driver 3, the information of the emotion determination of the driver 3, or the like, and stores the information in the storage portion 16.

Figure 5:
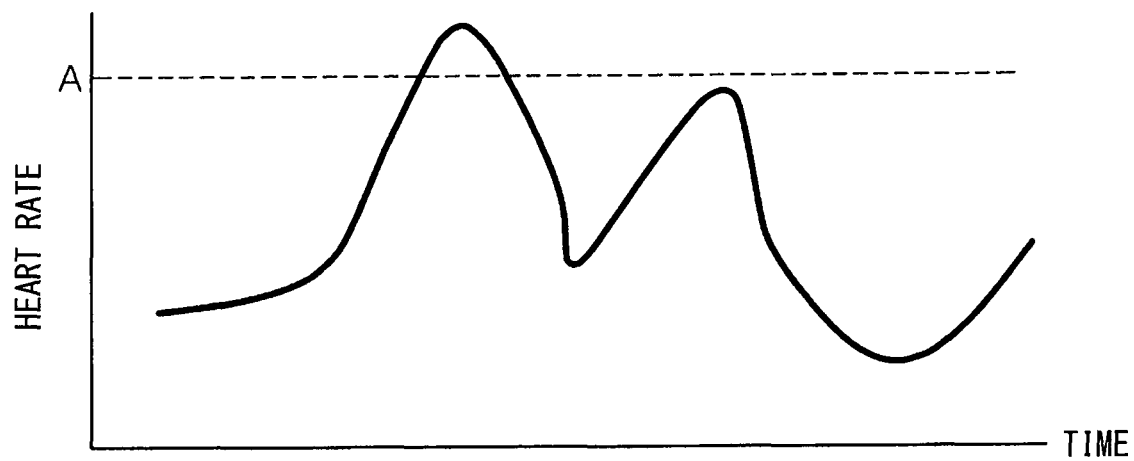
FIG. 5 is a diagram showing a change in heart rate detected by a wearable device.
Figure 6:
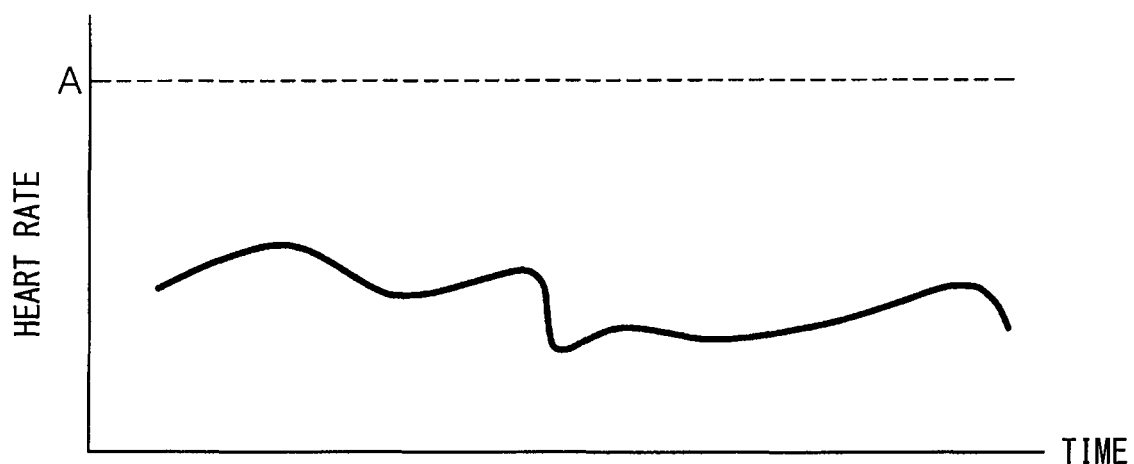
FIG. 6 is a diagram showing a change in heart rate detected by a different wearable device.

In S130, the control portion 17 of the vehicle device 7 determines whether the biometric information (for example, the heart rate) acquired from the wearable devices 4, 6 matches the biometric information (for example, the heart rate) acquired from the face image photographed by the compartment camera 2. In this case, for example, the heart rate detection data acquired from the wearable device 4 may change as shown in FIG. 5. The heart rate detection data acquired from the wearable device 6 may change as shown in FIG. 6. The time duration for detecting the heart rate by the wearable devices 4, 6 may be set from one minute to several minutes. In the time duration, the detection is performed for multiple times at a predetermined time interval (for example, time interval of one second, two seconds, or three seconds).

Figure 7:
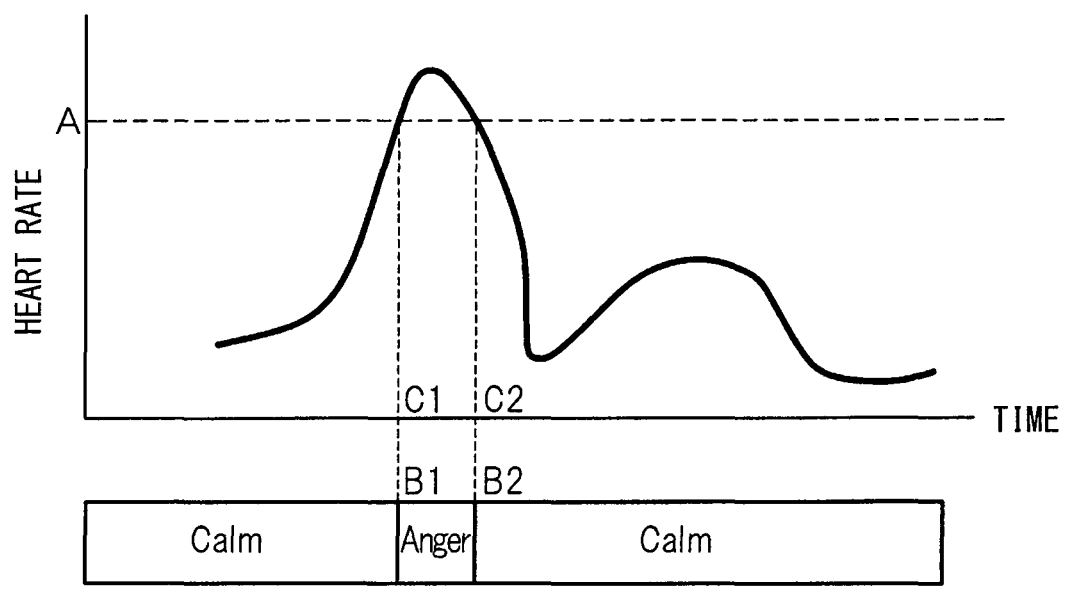
FIG. 7 is a diagram showing a change in heart rate detected based on a face image of a driver and a change in emotion determined based on the face image of the driver.

The heart rate data acquired from the face image photographed by the compartment camera 2 may change as shown in FIG. 7. In this case, the face image may be successively photographed at a predetermined time interval in a time duration from one minute to several minutes. Comparing FIG. 5, FIG. 6, and FIG. 7, there is a part where the heart rate exceeds a predetermined threshold A in FIG. 5 and FIG. 7, so that it is determined that the heart rate graph in FIG. 5 matches the heart rate graph in FIG. 7.

The emotion determination information of the driver 3 acquired based on the face image photographed by the compartment camera 2 is compared with the information of the heart rate acquired from the wearable devices 4, 6. The comparison will be performed as described below. The emotion determination data acquired from the face image photographed by the compartment camera 2 may change as shown in FIG. 7. In this case, the face image may be successively photographed at a time interval in a time duration. The time interval may be set for one second, two seconds, or three seconds. The time duration may set from one minute to several minutes. In this case, in FIG. 7, the boundary from "Calm" to "Anger" is defined as a point B1 and the boundary from "Anger" to "Calm" is defined as a point B2. In FIG. 7 showing the change in the heart rate of the driver 3 acquired based on the face image photographed by the compartment camera 2, the intersection points of the heart rate graph and the threshold value A may be defined as points C1, C2. In this case, the point B1 almost matches the point C1, and the point B2 almost matches the point C2. Comparing FIG. 5, FIG. 6, and FIG. 7, there is a part where the heart rate exceeds a predetermined threshold A, that is, a part of "Anger" as the emotion determination in FIG. 5 and FIG. 7, so that it is determined that the heart rate graph in FIG. 5 matches the emotion diagram in FIG. 7.

In S130, the control portion 17 of the vehicle device 7 determines that there is the biometric information acquired from the wearable device 4 that matches the biometric information acquired from the face image photographed by the compartment camera 2 (S130:YES), the procedure proceeds to S140. In S140, the control portion 17 of the vehicle device 7 identifies the wearable device 4 having the matched biometric information as the wearable device 4 of the driver 3. In S150, the control portion 17 of the vehicle device 7 performs the association processing between the identified wearable device 4 and the driver 3. In this case, the control portion 17 of the vehicle device 7 analyzes multiple feature points in the face image photographed by the compartment camera 2, and stores the analyzed data of the shape or the position of each of the multiple feature points in the storage portion 16 as the personal data of the driver 3. The control portion 17 of the vehicle device 7 associates the personal data of the driver 3 with the ID data of the wearable device 4, and stores the personal data in the storage portion 16.

In S160, the control portion 17 of the vehicle device 7 activates an application program that executes a predetermined processing using the biometric information of the driver 3. In this case, an application program that urges the driver to pay attention to the safe driving using the heart rate or the like of the driver 3 may be executed. Then, the control ends.

In S130, when the control portion 17 of the vehicle device 7 determines that there is no biometric information acquired from the wearable device 4 that matches the biometric information acquired from the face image photographed by the compartment camera 2, the control portion 17 of the vehicle device 7 does not activate the application program and the control ends.

Figure 8A:
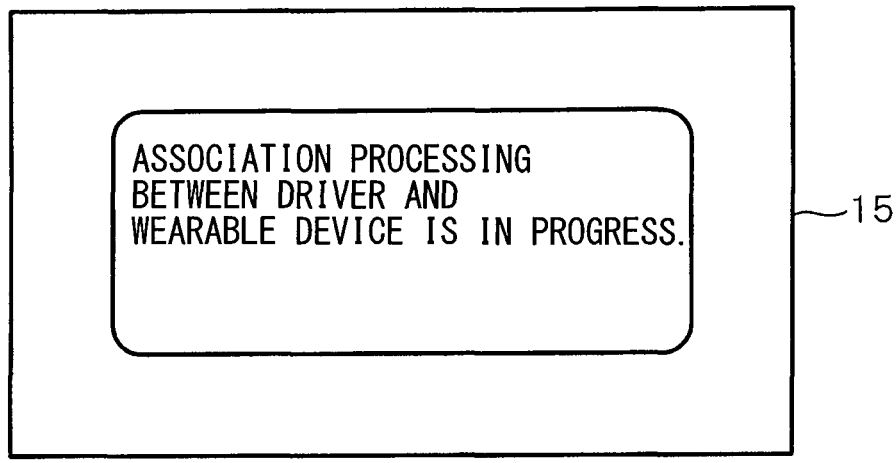
FIG. 8A is a diagram showing an example of content displayed on a display portion during an association processing.
Figure 8B:
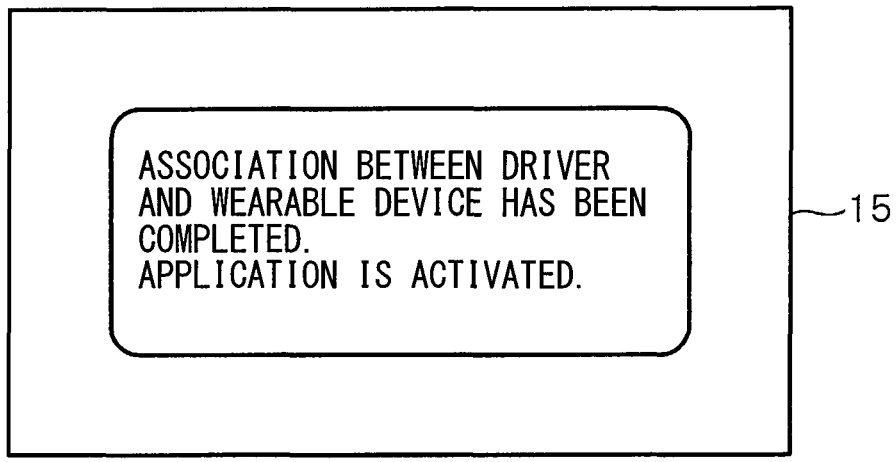
FIG. 8B is a diagram showing an example of content displayed on the display portion during the association processing.
Figure 8C:
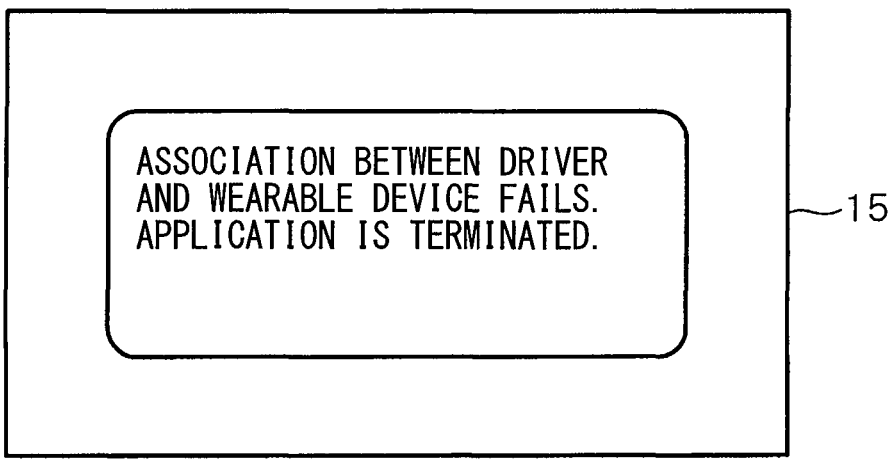
FIG. 8C is a diagram showing an example of content displayed on the display portion during the association processing.

Further, in the present embodiment, the association processing between the driver 3 and the wearable device 4 shown in FIG. 4 may start. In this case, as shown in FIG. 8A, the control portion 17 of the vehicle device 7 displays a message "Association processing between driver (that is, the driver 3) and wearable device (that is, the wearable device 4) is in progress." on the display portion 15. The association processing may succeed and the process in S150 is finished. In this case, as shown in FIG. 8B, the control portion 17 of the vehicle device 7 displays a message "Association between driver and wearable device has been completed. Application is activated." on the display portion 15. The association processing may fail, that is, in S130, the control portion 17 of the vehicle device 7 may determine that there is no biometric information acquired from the wearable device 4 that matches the biometric information acquired from the face image photographed by the compartment camera 2. In this case, as shown in FIG. 8C, the control portion 17 of the vehicle device 7 displays a message "Association between driver and wearable device fails. Application is terminated." on the display portion 15.

In the above-described configuration of the present embodiment, the video processing portion 14 of the vehicle device 7 receives the image data transmitted from the compartment camera 2 photographing the driver 3, analyzes the received image data, and detects the heart rate of the driver 3. The control portion 17 of the vehicle device 7 compares the biometric information transmitted from the one or more wearable devices 4, 6 possessed by the one or more people in the vehicle with the heart rate of the driver 3 detected by the video processing portion 14, and identifies the wearable device 4 possessed by the driver 3. Thus, even when the multiple wearable devices 4, 6 are brought into the vehicle, the configuration can determine the wearable device 4 possessed by the driver 3.

In the above-described embodiment, after identifying the wearable device 4 possessed by the driver 3, the control portion 17 of the vehicle device 7 associates the driver 3 with the wearable device 4. The control portion 17 of the vehicle device 7 stores the association information in the storage portion 16, and activates the application program that executes the predetermined processing using the biometric information of the driver 3. The association information may include the personal data of the driver 3, the personal identification information, or the ID information of the wearable device 4. Thus, after the control portion 17 of the vehicle device 7 stores the association information, the configuration can quickly determine the wearable device 4 possessed by the driver 3 based on the association information (for example, ID of the wearable device 4). The application program is automatically activated, so that the configuration can automatically execute the predetermined processing using the biometric information of the driver 3.

In the above-described embodiment, the vehicle device 7 is wirelessly connected to the wearable devices 4, 6 brought into the vehicle. When there is the wearable device 4 associated with the driver 3, the vehicle device 7 determines whether the driver 3 associated with the wearable device 4 is sitting in the driver's seat. When the vehicle device 7 determines that the associated driver 3 is sitting in the driver's seat, the configuration can activate the predetermined processing using the biometric information of the driver 3. With this configuration, when the multiple wearable devices 4, 6 are brought into the vehicle, the vehicle device 7 can accurately and quickly determine the wearable device 4 possessed by the driver 3. Further, the vehicle device 7 can automatically activate the application program that executes the predetermined processing using the biometric information of the driver 3.

In the above-described embodiment, the compartment camera 2 transmits, but are not limited to, the face image of the driver 3 photographed by the compartment camera 2 to the vehicle device 7, and the vehicle device 7 analyzes the face image of the driver 3. Alternatively, the compartment camera 2 may analyze the photographed face image of the driver 3, and transmit the analyzed result information, that is, the heart rate information of the driver 3, the emotion determination information of the driver 3, the personal data information of the driver 3, or the like to the vehicle device 7. In the above-described embodiment, the vehicle device 7 is, but are not limited to, provided by the car navigation device. Alternatively, the vehicle device 7 may be provided by another vehicle device.

While the disclosure has been described with reference to preferred embodiments thereof, it is to be understood that the disclosure is not limited to the preferred embodiments and constructions. The disclosure is intended to cover various modification and equivalent arrangements. In addition, the various combinations and configurations, which are preferred, other combinations and configurations, including more, less or only a single element, are also within the spirit and scope of the disclosure.

The invention claimed is:

1. A vehicle device comprising a processor configured to:
receive image data transmitted from a compartment camera that photographs a driver;
analyze the image data received from the compartment camera;
detect a heart rate of the driver based on the image data;
wirelessly communicate with one or more wearable devices possessed by one or more people who ride on a vehicle;
determine whether the one or more wearable devices include a wearable device that has been registered together with image data of a person;
identify, when the process does not determine that the one or more wearable devices include the wearable device that has been registered, a wearable device, among the one or more wearable devices, possessed by the driver by comparing biometric information transmitted from the one or more wearable devices with the heart rate of the driver, and register the identified wearable device together with the image data of the driver;
identify, when the processor determines that the one or more wearable devices include the wearable device that has been registered, that the person registered with the registered wearable device is seated on a driver seat by comparing the registered image data of the person with the image data transmitted from the compartment camera; and
activate, when the processor identifies the wearable device possessed by the driver or identifies that the person registered with the registered wearable device is seated on the driver seat, an application program using the biometric information of the driver.

2. The vehicle device according to claim 1, wherein the processor is further configured to:
determine an emotion of the driver by analyzing the image data received from the compartment camera; and
identify the wearable device possessed by the driver by comparing the biometric information transmitted from the one or more wearable devices with the emotion of the driver.

3. The vehicle device according to claim 1, wherein the processor is further configured to:
determine whether there is the wearable device associated with the driver in the one or more wearable devices by communicating with the one or more wearable devices; and
activate an application program that executes a predetermined processing using the biometric information of the driver when the processor determines that there is the wearable device associated with the driver.

4. The vehicle device according to claim 1, wherein the processor is further configured to:
determine whether there is the wearable device associated with the driver in the one or more wearable devices by communicating with the one or more wearable devices;
determine whether the driver associated with the wearable device sits in a driver seat; and
activate the application program that executes a predetermined processing using the biometric information of the driver when the processor determines that there is the wearable device associated with the driver and the processor determines that the driver associated with the wearable device sits in the driver seat.

\* \* \* \* \*